(12) United States Patent
Pis et al.

(10) Patent No.: US 7,655,806 B2
(45) Date of Patent: Feb. 2, 2010

(54) PROCESS FOR PURIFICATION OF ANASTROZOLE

(75) Inventors: Jaroslav Pis, Prague (CZ); Rudolf Smrz, Prague (CZ)

(73) Assignee: Synthon BV, Nijmegen (NL)

( * ) Notice: Subject to any disclaimer, the term of this patent is extended or adjusted under 35 U.S.C. 154(b) by 0 days.

(21) Appl. No.: 11/750,781

(22) Filed: May 18, 2007

(65) Prior Publication Data

US 2007/0281982 A1    Dec. 6, 2007

Related U.S. Application Data

(60) Provisional application No. 60/747,787, filed on May 19, 2006.

(51) Int. Cl.
*C07D 249/08* (2006.01)

(52) U.S. Cl. .................. 548/269.2; 548/262.2

(58) Field of Classification Search ............. 548/262.2, 548/269.2
See application file for complete search history.

(56) References Cited

U.S. PATENT DOCUMENTS

| 4,935,437 A | 6/1990 | Edwards et al. |
| RE36,617 E | 3/2000 | Edwards et al. |
| 2006/0035950 A1 | 2/2006 | Alnabari et al. |
| 2006/0189670 A1 | 8/2006 | Khile et al. |
| 2008/0076933 A1 | 3/2008 | Benes et al. |

FOREIGN PATENT DOCUMENTS

| EP | 0 296 749 B1 | 10/1994 |
| WO | WO 2005/105762 A1 | 11/2005 |
| WO | WO 2006/000836 A1 | 1/2006 |

*Primary Examiner*—Kamal A Saeed
*Assistant Examiner*—Samantha L Shterengarts
(74) *Attorney, Agent, or Firm*—Mark R. Buscher

(57) ABSTRACT

Anastrozole can be purified by crystallization from an aqueous-based solvent system. The aqueous-based solvent system can contain dilute acid, or an alcohol or both.

28 Claims, No Drawings

PROCESS FOR PURIFICATION OF ANASTROZOLE

This application claims the benefit of priority under 35 U.S.C. § 119(e) from U.S. provisional patent application No. 60/747,787, filed May 19, 2006, the entire contents of which are incorporated herein by reference.

The present invention relates to a process for purifying the compound anastrozole, such as to a pharmaceutically acceptable grade of purity.

BACKGROUND OF THE INVENTION

Anastrozole, chemically (2,2'-[5-(1H-1,2,4-triazol-1-ylmethyl)-1,3-phenylene]di(2-methylpropionitrile) of the formula (1)

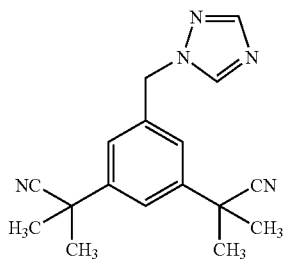

(1)

is a pharmaceutically active agent acting as a selective non-steroidal aromatase inhibitor. Aromatase is an enzyme which regulates the level of certain female sex hormones, such as estrogens.

In pharmaceutical applications, anastrozole is used for the treatment of advanced breast cancer in post-menopausal women. In the pharmaceutical compositions it is used in the form of the free base.

The whole class of 1,3-substituted aralkyl heterocyclic compounds, among which the anastrozole compound was a specific example, as well as acid addition salts of these compounds such as hydrochloride, hydrobromide, sulfate, nitrate, phosphate and toluene-p-sulfonate (these salts having not been exemplified in case of anastrozole), have been disclosed in U.S. Pat. No. 4,935,437 (reissued as US RE 36,617) and the EPB 296749.

There are various processes known for the synthesis of the anastrozole. The most important of them use the 1,2,4-triazole as it is a cheap and useful reagent. In the original document, U.S. Pat. No. 4,935,437, the anastrozole compound itself was actually prepared by two such procedures.

The first procedure (see Example 1 of EPB 296749) comprises, in the last steps, a reaction of the methyl compound of the formula (2) with N-bromosuccinimide to yield the bromomethyl-compound of the formula (3), which was treated with sodium 1,2,4-triazole to give the crude anastrozole.

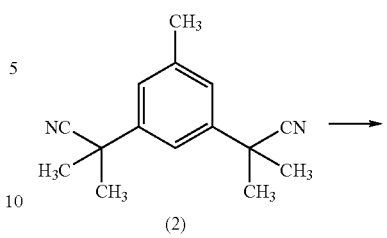

(2)

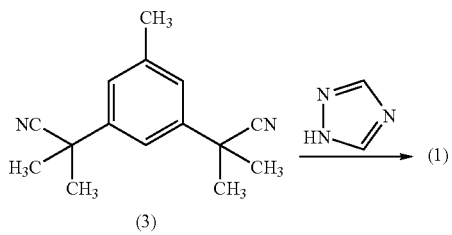

(3)

Crude anastrozole was purified by column chromatography (details not given) and crystallization from cyclohexane/ethyl acetate got a purified material with a melting point of 81-82° C. Neither the yield nor the purity is mentioned in the process description. In a later document WO 2005-105762, it is reported that this process was repeated with a poor yield (<50%) and poor quality (<90% by HPLC). In particular, the crystallization procedure was not successful in reducing the level of the isomeric impurity—the isoanastrozole of the formula (4),

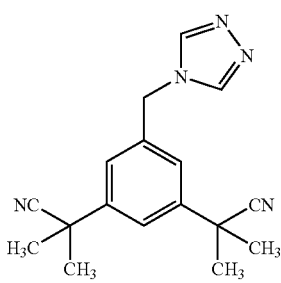

(4)

which was still contained in a level of more than 1.0% by HPLC.

In a second procedure disclosed in the EPB'749 (Example 8), the last steps use the hydroxymethyl-compound of formula (5), which was converted into a chloromethyl-compound of formula (6). The crude compound (6) (obtained by evaporation of the ethyl acetate extract of the reaction mixture) was reacted with 1,2,4-triazole for 18 hours at the reflux in acetonitrile to yield a mixture of anastrozole and the isoanastrozole of the formula (4). This mixture was separated by column chromatography using methanol-chloroform mixture as the eluent. Also, the yield and the purity of the anastrozole product was not mentioned.

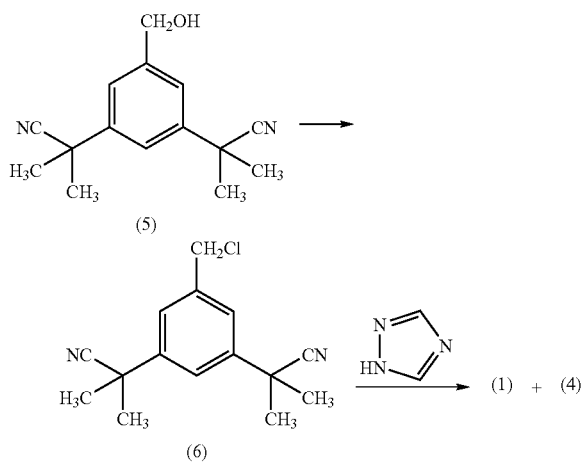

The need to use chromatographic separation makes these processes economically unattractive for industrial scale.

One way to avoid this problem is to use a different synthetic scheme; one that does not produce the isoanastrozole compound and/or produces impurities that are easy to remove. Some regioselective schemes are known; see for example EPB '749 example 69 and WO 2006-000836, which essentially avoid the production of isoanastrozole. But these schemes have disadvantages including the use of expensive and/or toxic reagents and conditions or the requirement of extra synthetic steps. Improving the 1,2,4-triazole process would thus be desirable.

Two later documents were published dealing with attempts to improve the above 1,2,4-triazole-employing process, and in particular with attempts to provide a pharmaceutical grade anastrozole (which is a compound having at least 99.7% purity with max. 0.1% of any single impurity) without the need of a chromatographic purification of the crude anastrozole.

WO 2005-105762 indicates that the known process provides a product with 3-5% of the isoanastrozole impurity (4) when performing the process on an industrial scale. The level of the impurity may be reduced by using dimethyl formamide ("DMF"), advantageously in combination with a non-polar solvent in the coupling reaction. But, the isoanastrozole impurity cannot be removed to <0.1% level by any crystallization technique, even after a repeated crystallization. However, such impurity may be reduced to the <0.1% level by crystallizing an anastrozole salt. After the purification, the required base of anastrozole is obtained by neutralization of the salt.

The overall process of WO 2005-105762 can be summarized as follows:
- reacting the bromo-compound (3) with sodium or potassium 1,2,4-triazole in DMF with or without a non-polar solvent;
- quenching the reaction mixture with water medium and extracting crude anastrozole with an organic solvent;
- distilling the organic solvent and treating the rest with organic or mineral acid to form the acid addition salt of anastrozole;
- recrystallizing the acid addition salt from an organic solvent;
- neutralization of the salt with a base to obtain anastrozole; and
- crystallizing the anastrozole from an organic solvent to get a product of pharmaceutically acceptable grade.

US 2006-0035950 reports a similar process for the purification of crude anastrozole. The process employs the bromide intermediate (3) as a starting material and has the following characteristics:
- the intermediate (3) is preferably purified before its use in the synthesis by crystallization or precipitation;
- the coupling of (3) with the sodium 1,2,4-triazole or with the 1,2,4-triazole under basic conditions yielding crude anastrozole is performed in a solvent of the Class 3 or Class 2 (as defined in the Industrial guideline of residual solvents published by the International Conference of Harmonization); and
- the crude anastrozole is purified via an isolated anastrozole salt form involving crystallization, acidic extraction, or both.

The isolated salt form of anastrozole, e.g., as the hydrochloride or hydrobromide salt, is crystallized from an organic solvent or mixtures of the organic solvents (similarly as in WO 2005-105762). The purified salt is then converted back to the desired anastrozole base by neutralization. In the examples, the neutralization is achieved by adding an aqueous solution of an inorganic base (sodium carbonate) and the liberated anastrozole base is extracted into an organic solvent (e.g. toluene) and crystallized therefrom.

Although this crystallization removes most of the impurities, particularly hydrophobic impurities, the published application reports that the isoanastrozole impurity is not sufficiently reduced. In fact, various solvents employed for the crystallization of the anastrozole hydrochloride provided a product having from 1.1 to 8.1% of isoanastrozole. To overcome this, the published application proposes selectively extracting impurities, especially the isoanastrozole, via an acidic solution.

Specifically, a crude anastrozole (base) in an organic solvent is mixed with an aqueous acid solution having a pH between 0.7 to 1.7, whereby the isoanastrozole is selectively removed into the aqueous phase leaving most of the desired anastrozole in the organic phase (however a part of the anastrozole is also removed into the aqueous phase as the reported yield of the single extraction is max. 82%). Upon phase separation and removal of the aqueous phase, the anastrozole-containing organic phase has less isoanastrozole. The extraction may be performed multiple times in order to reach a desired level of isoanastrozole. Contrary to the first process, this process does not efficiently remove hydrophobic impurities.

Therefore, both processes may be advantageously combined: the anastrozole is purified by extraction, then it is converted into the salt, the salt is isolated (whereby it is purified from hydrophobic impurities) and then converted back to the anastrozole base. However, it appears from the examples that multiple acidic extractions are needed in order to adequately reduce the level of isoanastrozole.

In summary, it can be quite difficult to remove impurities from crude anastrozole sufficiently to obtain a pharmaceutically acceptable quality grade. It would be desirable to have an alternative purification process. In particular, a reliable process that can be shorter/simpler and especially cheaper/more efficient would be advantageous.

SUMMARY OF THE INVENTION

The present invention is based on the discoveries that anastrozole can be crystallized from water or a water-containing solvent system and that such crystallizations can dramatically increase the purity of anastrozole. Accordingly, a first aspect of the invention provides a process which comprises crystallizing anastrozole base from an aqueous-based solvent system that contains anastrozole and/or its ion dissolved therein. The aqueous-based solvent system can be simply water, but typically further comprises at least one of a water miscible C1-C4 aliphatic alcohol such as methanol, a dipolar aprotic solvent, and an acid such as hydrochloric acid. The term "aqueous-based" is not intended to mean that water must comprise the majority of the solvent system, however, as minor amounts, typically at least 20 vol. %, are also contemplated. The dipolar aprotic solvent, when present, is typically an artifact of the synthesis of anastrozole; i.e., it is the solvent in the crude reaction mixture from which anastrozole is desired to be crystallized. When not isolating anastrozole from a crude reaction mixture, the aqueous-based solvent system typically contains water and at least one of the acid or the alcohol and often both.

Another aspect of the invention relates to a process for the purification of anastrozole which comprises combining anastrozole base with an aqueous acid solution to form a solution and crystallizing anastrozole base from the solution. Although an acid is present, an anastrozole acid addition salt is not precipitated. As explained more fully hereinafter, it is believed that the acid forms a salt with anastrozole allowing for better water solubility, but due to hydrolytic instability and the severe water insolubility of the base, the free base of anastrozole can precipitate instead of the anastrozole salt unless a large excess of acid is present. Accordingly the acid solution is generally a dilute acid, usually having an acid concentration of 5% or less, frequently 1-2%. A useful acid is HCl. The use of an aqueous acid solution as, or as part of, the aqueous-based solvent system allows for significant purity increases in the anastrozole crystallization, especially with respect to the isoanastrozole impurity. The aqueous acid solution can further contain a water miscible C1-C4 aliphatic alcohol as mentioned above. The preferred alcohol is methanol. Generally the amount of alcohol present in an aqueous acid solution is no greater than 80% and typically is present within a range of 20-80%, and in some embodiments 40-60%.

A further aspect of the present invention relates to a process for the purification of anastrozole that comprises combining anastrozole base, water, and a water miscible C1-C4 aliphatic alcohol, preferably methanol, to form a solution and crystallizing anastrozole base from the solution. The alcohol is generally present within a range of 20-80%, preferably 40-60%, with the balance being water. An acid is normally not present in this embodiment. Crystallizing the anastrozole from this aqueous-based solvent system improves the purity of the anastrozole.

An additional aspect of the invention relates to a process for purifying anastrozole, which comprises:

(a) recrystallizing anastrozole base from an aqueous-based solvent system that comprises water, hydrochloric acid, optionally a water miscible C1-C4 aliphatic alcohol, and optionally a dipolar aprotic solvent; and/or (b) recrystallizing anastrozole base from an aqueous-based solvent system that comprises water and a water miscible C1-C4 aliphatic alcohol, but does not contain hydrochloric acid.

The recrystallization steps can be performed in any order and each can be performed multiple times; e.g. performing steps (a), (a), (b), (a) and (b). However, typically such a large number of recrystallization steps are not needed to obtain a desired pharmaceutical purity level. The use of both an acid-containing aqueous-based solvent system and a non-acid containing aqueous based solvent system to carry out the recrystallizations of anastrozole can provide an efficient complementary purification effect.

A further aspect of the invention relates to a process for making a pharmaceutical grade anastrozole comprising the steps of:

a) providing anastrozole in a reaction mixture by the condensation of the chloromethyl-compound of the formula (6) or bromomethyl-compound of formula (3) with sodium 1,2,4-triazole in a water miscible dipolar aprotic solvent;

b) adding water and hydrochloric acid to the anastrozole-containing reaction mixture and precipitating crude anastrozole base therefrom;

c) dissolving said crude anastrozole base in a mixture of water and a water miscible C1-C4 aliphatic alcohol in the presence of max. 1.5 molar equivalents of HCl and crystallizing anastrozole base to form purified anastrozole; and d) recrystallizing one or more times the purified anastrozole from a mixture of water and water miscible C1-C4 aliphatic alcohol to form anastrozole base in a purity of at least 99.97% and less than 0.1% of isoanastrozole.

DETAILED DESCRIPTION OF THE INVENTION

The present invention can purify anastrozole without the need to convert crude anastrozole into an isolated anastrozole acid addition salt and/or to employ extraction steps in a process of purification of the crude anastrozole resulting from the synthetic process employing the 1,2,4-triazole and a halomethyl-reaction partner. Instead, one of two simple crystallization processes may be employed, alone or in combination, whereby any of them allows to decrease not only the content of the isoanastrozole impurity of formula (4) but also other impurities arisen from the synthesis. As a result, a pharmaceutical grade anastrozole, i.e. anastrozole having the content of the title compound of at least 99.7% and the content of any single structurally related impurity of less than 0.1%, may be obtained in a simple and reliable process on an industrial scale.

The first crystallization process of the present invention is based on the finding that acid addition salts of anastrozole are very sensitive towards aqueous hydrolysis. Dissolving or suspending an anastrozole salt, e.g. anastrozole hydrochloride, in an aqueous environment results in forming the solid anastrozole base without a need of any neutralization agent. This is most probably because anastrozole base itself is a very week base (so that the equilibrium content of the non-protonated anastrozole in the acidic environment is relatively high) and, moreover, the anastrozole base is extremely insoluble in water. Thus, the hydrolytic equilibrium is dramatically shifted towards the formation of anastrozole base, which, as an insoluble product, precipitates from the aqueous environment and further shifts the equilibrium towards its formation. Apparently the salt can only be stabilized in the presence of sufficient excess (generally more than 2 molar equivalents) of the corresponding acid in the aqueous environment. Some salts may be isolated, e.g. crystallized, from such a system depending on the solubility and concentration of the salt and if the excess amount of the acid is sufficiently high.

The above finding has an important implication in that the anastrozole base cannot be converted into the equivalent amount of the anastrozole salt when placed into an aqueous environment comprising dilute acid, and, due to its limited solubility, it preferably remains in such system in the undissolved state and as a base. Accordingly, even though the solution may contain anastrozole salt (e.g. ionic anastrozole), anastrozole can be crystallized from the dilute aqueous acidic solutions as the base and not as the corresponding salt as one would expect.

Surprisingly, the crystallization of anastrozole under these conditions is accompanied with a substantive purification effect superior to the known purification techniques. More than 75% of the original isoanastrozole present may be removed within a single crystallization.

In particular, the amount of the acid in the diluted acidic solution is usually from 0.1 to 2 molar equivalents, more typically 0.1 to 1.5 molar equivalents, in respect to anastrozole. In terms of concentration, the acid is normally less than 5%, preferably less than 2% (e.g. 1%-2%) based on the amount of water present in the solvent system. The preferred acid is hydrochloric acid. However, it should be understood that hydrochloric acid is only an example of a suitable acid useful in the inventive process and the invention is by no way limited to using this acid only.

In addition to water, the aqueous acidic solution of anastrozole may also contain an aliphatic water miscible C1-C4 alcohol, such as methanol, ethanol or isopropanol. Generally such an alcohol is not present in amounts greater than 80%, and more typically 20%-80%, preferably 40%-60%. In the acid-containing embodiments of the solvent system that further comprise the anastrozole reaction solvent, the alcohol is typically used in amounts less than 30% such as 1%-20%, typically 5% to 10% based on the total volume of the solvent system. For clarity, water in the acid-containing solvent systems typically comprises, for practical reasons, at least 20% of the solvent system and more typically at least 30% and preferably 40%-100%. Generally the water accounts for 20%-80%, typically 40%-60%, with the remainder being the alcohol and/or water miscible reaction solvent such as DMF or DMA.

As a second embodiment of the invention, anastrozole may be crystallized from a mixture of water and a water miscible aliphatic alcohol, wherein the concentration of the alcohol is from about 20 to about 80% of the overall volume of the solvent mixture. The preferred alcohol is methanol and the preferred concentration is from 40 to 60%, most preferably 50% in respect to the total volume of the solvent mixture. Generally no acid is present in this solvent mixture, though it is not necessarily excluded.

Contrary to the teaching in the prior art (that no crystallization process may be effective for the purpose of the purification of anastrozole base), this crystallization solvent system provides an efficient decrease in both the amount of the isoanastrozole and the other structurally related impurities. This crystallization procedure has a slightly lower purification effect in respect to the isoanastrozole than that disclosed above, however, it is more efficient in removing the other structurally related impurities.

Both of the crystallization procedures can be performed by a classical crystallization technique(s), e.g., by heating the mixture up to the dissolution and cooling it under precipitation of the solid. To improve the crystallization, it is useful to inoculate the mixture by a seeding crystal of anastrozole during cooling, and it is also useful to dilute the mixture with water after the precipitation has started to enhance the yield.

In particular, by using the above inventive processes in an efficient combination, the invention allows to provide pharmaceutical grade anastrozole. A particularly preferred arrangement in combination with anastrozole synthesis is described below.

The first step of the process provides the anastrozole-comprising reaction mixture. The reaction mixture comprising the anastrozole molecule is provided according to any known principle, but preferably by the condensation of the bromomethyl-compound of the formula (3) or the chloromethyl-compound of the formula (6) with 1,2,4-triazole. These starting materials are either commercially available or may be made according to processes known in the art. Preferably, the starting compounds are charged in a purified state. While the purification of the bromo-compound (3) has been sufficiently disclosed in the prior art, there is no method known for the purification of the chloro-compound (6). It has been found, however, that the compound (6) may be efficiently purified by a crystallization from an alcoholic solvent, e.g. from isopropanol, without a danger of the reaction of the reactive chlorine in the compound (6) with the solvent.

The 1,2,4-triazole is advantageously charged as its sodium or potassium salt, or together with an alkali metal- or an alkali earth metal containing base (such as potassium carbonate or sodium methoxide). In a particular aspect, which is important in relation to the further isolation process, the reaction is performed in a water miscible solvent, preferably in a water miscible dipolar aprotic solvent, and most preferably in dimethyl formamide or dimethyl acetamide. Thus, the organic co-solvents recommended by WO 2005-105762 are preferably not necessary, which makes the process simpler and ecologically friendlier.

As known in the art, the anastrozole-forming condensation of 1,2,4-triazole with the halomethyl reaction partner is accompanied with a side reaction yielding the positional isomer of anastrozole, i.e., the isoanastrozole of formula (4). In addition, other impurities may be formed and/or remainder of the starting materials may be present due to the incompleteness of the conversion.

In general, about 5-10% of the isoanastrozole is usually formed in the reaction mixture before starting any process of isolation and purification. The original reaction mixture may also comprise up to 10% or more of the structurally related impurities arising from the synthesis in this and/or preceded synthetic steps.

In the second step of this process, the crude anastrozole base is precipitated from the reaction mixture by using a dilute aqueous acid. The reaction mixture of the first step is diluted by water (using advantageously 1-2 volumes in respect to the volume of the original mixture) and optionally filtered, such as with an activated carbon. As no immiscible organic solvents are employed, a clear solution comprising anastrozole is obtained.

The anastrozole-comprising solution is then treated with aqueous hydrochloric acid, preferably at a temperature from 35° to 65° C. The amount of the hydrochloric acid is selected such that it typically comprises from 0.1 to 2 molar equivalents of HCl and the concentration of HCl is less than 5%, preferably less than 2% of the total mass of the water. Then the solution (e.g. the aqueous-based solvent system containing anastrozole and/or its ion) is cooled to a temperature not exceeding 25° C. In accordance with the invented feature, anastrozole does not remain in the solution under these conditions as the dissolved anastrozole hydrochloride, but precipitates as the anastrozole base. To facilitate the crystallization, it is advantageous to seed the reaction mixture by a small amount of crystals of anastrozole base. Furthermore it is useful to dilute the reaction mixture by adding additional water after the precipitation has started (frequently an approx. equal volume as was the original volume of the mixture), to increase the yield and improve the purification effect.

The precipitate is isolated by filtration by conventional means and optionally washed and dried to yield crude anastrozole base. The crude product comprises in general around 2% of the isoanastrozole impurity, or about 20% of its original content in the reaction mixture.

In the third step, the crude anastrozole base is purified by crystallization from a solution comprising dilute aqueous acid. In an advantageous mode, the crude anastrozole base is suspended in a mixture of water and a water-miscible C1-C4 aliphatic alcohol, which is, e.g., methanol, ethanol, isopropanol and/or mixtures thereof. The presence of the alcohols improves the purification effect and increases the solubility, thus decreasing the overall volume of the crystallization mixture. To this mixture, aqueous hydrochloric acid is added and the mixture is heated until dissolution. The concentration of the alcohol is typically from 20-80 vol % of the water-alcohol mixture, more preferably from 40 to 60 vol %. The alcohol is typically methanol. The amount of the acid preferably does not exceed 2 molar equivalents, typically not more than 1.5 molar equivalents, in respect to anastrozole. The temperature of heating is from 40° to 60° C.

The solution is then subjected to crystallization by cooling it to a temperature of less than 25° C. The crystallization is preferably facilitated by seeding the mixture during cooling by adding a small amount of crystals of anastrozole base. Furthermore, the crystallization mixture may be also subsequently diluted by water (e.g., by an approx. equal volume as was the original volume of the mixture).

The precipitate is isolated by filtration by conventional means and optionally washed and dried to yield purified anastrozole base.

The purified anastrozole generally comprises less than 0.5% of isoanastrozole impurity. If this limit is not reached, it is advantageous to repeat this third step until the limit is reached. In average, no repetition is generally needed.

In the fourth step, the purified anastrozole base is crystallized from an alcohol-water mixture.

The purified anastrozole base is suspended in a mixture of water and a water-miscible aliphatic alcohol, which is, e.g. methanol, ethanol, isopropanol and/or mixtures thereof, and the mixture is heated until dissolution. The concentration of the alcohol is generally from 20-80 vol % of the water-alcohol mixture, and typically from 40 to 60%. The alcohol is generally methanol. The temperature of heating is usually from 40° to 60° C. If necessary, the warm solution may be filtered with an activated carbon.

The solution is then subjected to crystallization by cooling it to a temperature of less than 25° C. The crystallization is advantageously facilitated by seeding the mixture during cooling with a small amount of crystals of anastrozole base. Furthermore, the crystallization mixture may be also subsequently diluted by water (e.g., by an approx. equal volume as was the original volume of water or higher).

The precipitate is isolated by filtration by conventional means and optionally washed and dried to yield anastrozole base generally of pharmaceutically acceptable grade. If the product does not correspond with the limits for the pharmaceutical grade anastrozole, the fourth step may be repeated. In general, the process of the fourth step is carried out twice.

The effectiveness of the process has been seen in several kilogram scale production batches, which can be summarized by the following illustrative data.

|  | Reaction mixture | Crude Product | Purified Anastrozole | After the fourth step | |
|---|---|---|---|---|---|
|  |  |  |  | 1st repetition | 2nd repetition |
| Content of (4) | 10% | 2% | 0.45% | 0.15% | 0.07% |
| Sum of other impurities. | 2% | 1% | 0.5% | 0.2% | 0.1% |

In comparison with the extraction process reported in the prior art, it appears that 10 extractions or more may be necessary to obtain the product of the same quality as shown above.

In general, the yield of the overall process, calculated on the amount of the starting compound (3), is around 60 to 70%. The purification process does not require any extraction step. It may be easily performed in multi-kilogram scale on single equipment.

The invention is further illustrated by the following examples.

EXPERIMENTAL EXAMPLE 1

Stability of Anastrozole Base in a Dilute Aqueous Hydrochloric Acid 0.5 g of anastrozole base was suspended in 10 ml of distilled water at r.t. and under stirring. 0.155 ml (1.1. eq.) of conc. hydrochloric acid was added under stirring. The mixture was stirred for 1 hour at room temperature, the solid was filtered, and washed by 5 ml of water. Dried on air at room temperature for 2 days.

Melting point (capillary) 82.6° C.
Structure: anastrozole base

EXPERIMENTAL EXAMPLE 2

Conversion of Anastrozole Base into Anastrozole Hydrochloride Under an Excess of Hydrochloric Acid 0.5 g of anastrozole base was suspended at room temperature and under stirring in 5 ml of 10% aqueous hydrochloric acid. A part of the solid has dissolved. For a complete dissolution, next 3 ml of the same acid were added and the mixture was heated to 42° C. The solution was filtered and the filter was washed with 2 ml of the same acid.

The solution was treated under stirring with 10 ml of distilled water at 20-25° C. and stirred for 30 minutes. The solution became turbid and crystalline product separated. The mixture was cooled to 5° C. and kept stirred for 1 hour. The solid was filtered, washed with 5 ml of water and dried on air.

Yield: 0.633 g of anastrozole hydrochloride (dihydrate).

EXPERIMENTAL EXAMPLE 3

Preparation and Hydrolysis of Anastrozole Hydrochloride in Water 1.0 g of anastrozole base was suspended in 10 ml of water and 2.5 ml of 1:1 hydrochloric acid was added. The resulted solution was filtered and the filter was washed with 5 ml of distilled water. The filtrate was poured on a Petri dish and allowed to evaporate on air for 3 days. Well developed crystals of anastrozole hydrochloride were formed with m.p. 107.7 C (capillary) 0.6-0.7 g of the so formed crystals were dissolved in minimal amount of water (about 2 ml) and 20 ml of water was slowly added under stirring. Crystalline product precipitated during adding the water. The mixture was stirred for 30 minutes and allowed to stand for 2 days. The crystals were filtered, washed by 10 ml of water and dried on air.

Resulted anastrozole base had the m.p. 83.5° C. (capillary).

Preparation 1

Synthesis and purification of α,α,α',α'-tetramethyl-5-chloromethyl-1,3-benzene diacetonitrile (compound of formula (6))

The reactor was charged with about 9.6 L of N,N-dimethylacetamide, 6 kg α,α,α',α' tetramethyl-5-hydroxymethyl-1,3-benzene diacetonitrile (compound of formula (5)) was added thereto and the mixture was stirred at about 25° C. until dissolution. After dissolution, the solution was cooled down to approx. 15° C. and 3.2 kg thionylchloride was gradually added over a period of 45-75 minutes at approx. 30° C. The reaction mixture was stirred for approx. 1-2 hours at 20 to 35° C.

18 l of water was added over a period of 15-30 minutes at about 20-25° C. The resulting suspension was stirred for 15-20 minutes at 20-25° C. and subsequently filtered. The filtercake was washed in portions with a total of 18 l of water. The pH of the last washing should be higher then 5. If not, washings are repeated with 3 l water.

The reactor was charged with 8.4 l 2-propanol and the crude solid product was added. The suspension was heated and stirred for approx. 15 min. at 80°-85° C. The reaction mixture was then cooled to approx. 20° C. and stirred for about 0.5 hours at 15°-25° C. The resulting suspension was filtered and the filtercake was washed in several portions with a total of 3 l of 2-propanol. This crystallization procedure was repeated once more and the crystals were subsequently dried.

Yield: approximately 5.6 kg (87%) of the title product.

EXAMPLE 1

Synthesis and Purification of Anastrozole

Step 1—Providing the Reaction Mixture Comprising Anastrozole

The reactor was charged with approx. 4.2 kg sodium methanolate solution (approx. 30%) and 1.6 kg 1,2,4-triazole. The mixture was stirred for about 15 minutes at 20°-30° C.

5.5 l of N,N-Dimethylacetamide was added and methanol was removed by distillation under reduced pressure at 50°-65° C.

11 l of N,N-Dimethylacetamide was added to the residue and the mixture was stirred at 15°-25° C.

5.5 kg of the Compound (6) was added. The reaction mixture was kept at 15 to 30° C. for approx. 1.5 hr and subsequently the reaction mixture was heated to 45°-55° C. and stirred for approx. 1.5 hrs.

Step 2—Precipitation of the Crude Anastrozole 16 l water was added to the mixture of Step 1 and the reaction mixture was heated to 45-55° C. Then a mixture of 0.3 kg activated carbon in 2 l water was added. The suspension was stirred for approx. 30 min at 45°-55° C. and subsequently filtered. The filtercake was washed with a mixture of 2 l methanol and 2 l water (40°-50° C.).

The filtrate was stirred and 1.7 l concentrated hydrochloric acid was gradually added.

The reaction mixture was cooled down to approx. 25° C. and innoculated with 20 g anastrozole. The mixture was cooled to 15-25° C. for 30 to 45 min and 38 l water was slowly added. The crystallization mixture was cooled to about 0° C. for 4 to 5 hours. The resulting suspension was filtered and washed with a cold mixture of 4 l methanol and 15 l water.

Step 3—Preparation of Purified Anastrozole

The product of the Step 2 was added under stirring to a mixture of 5.1 l methanol and 5.1 l water.

0.31 l of hydrochloric acid was added and the suspension was heated to 40°-50° C. until dissolution. The mixture was cooled down to approx. 20° C. During cooling, at a temperature of 30°-25° C., the mixture was seeded with 10 g anastrozole. The mixture was cooled to 15°-25° C. and 15 l water was added gradually. The mixture was cooled to about 0° C. and stirred for 5 to 6.5 hrs. The resulting suspension was filtered and washed with a cold mixture of 3.5 l methanol and 13 l water.

Step 4—Preparation of Pharmaceutical Grade Anastrozole

Crystallization 1

The product of the Step 3 was added under stirring to a mixture of 6.1 l methanol and 6.1 l water. The suspension was heated to 40-50° C. until dissolution. The reaction mixture was cooled to approx. 20° C. At about 30°-25° C., the mixture was seeded with 10 g anastrozole crude. The mixture was cooled to 15°-25° C. 6 l of water was added gradually and the mixture was stirred for 4 to 5 hrs. The resulting suspension was filtered and washed with a cold mixture of 3.5 l of methanol and 13 l of water. The filter cake was dried.

Yield: approximately 4.5 kg of Anastrozole Content of isoanastrozole <0.2% (HPLC).

Crystallization 2

The reactor was charged with 4 l of methanol and 4 l of water. 4.5 kg anastrozole from the Crystallization 1 was added. A suspension of 0.14 kg activated carbon in a mixture of 0.5 l methanol and 0.5 l water was added. The mixture was heated to 40°-50° C. until dissolution of anastrozole crude and stirred for approx. 30 min. Then the suspension of activated carbon was filtered and washed with a heated (35°-40° C.) mixture of 1.5 l methanol and 1.5 l water. The reaction mixture was cooled to approx. 20° C. At about 30°-25° C., the reaction mixture was seeded with 10 g anastrozole. The reaction mixture was cooled to 15°-25° C. 12 l water was added gradually and the mixture was stirred for 4 to 5 hrs. The resulting suspension was filtered and washed with a cold mixture of 3 l of methanol and 12 l of water. The filter cake was subsequently dried.

Yield: approximately 4.2 kg of Anastrozole of pharmaceutical grade quality.

Each of the patents and patent applications mentioned above are incorporated herein by reference. The invention having been described it will be obvious that the same may be varied in many ways and all such modifications are contemplated as being within the scope of the invention as defined by the following claims.

What is claimed:

1. A process, which comprises crystallizing anastrozole base from an aqueous-based solvent system that contains anastrozole and/or its ion dissolved therein.

2. The process according to claim 1, wherein said aqueous-based solvent system comprises water and at least one water miscible organic solvent.

3. The process according to claim 2, wherein said water miscible organic solvent is selected from the group consisting of dimethyl formamide, dimethyl acetamide, C1-C4 aliphatic alcohols, and mixtures thereof.

4. The process according to claim 1, wherein said aqueous-based solvent system further contains an acid dissolved therein.

5. The process according to claim 4, wherein said acid is hydrochloric acid.

6. The process according to claim 4, wherein the amount of acid is less than 5% based on the amount of water.

7. The process according to claim 4, wherein the amount of acid is less than 1.5 molar equivalents of anastrozole.

8. The process according to claim 1, wherein water comprises at least 20% of the total volume of the aqueous-based solvent system.

9. The process according to claim 2, wherein said solvent system consists of water and methanol.

10. The process according to claim 2, wherein said solvent system consists of water, dimethyl formamide, and optionally methanol, and wherein an acid is further dissolved in said solvent system in an amount not greater than 5% based on the amount of water.

11. A process for purification of anastrozole, which comprises:
combining anastrozole base with an aqueous acid solution to form a solution; and
crystallizing anastrozole base from said formed solution.

12. The process according to claim 11, wherein the acid is hydrochloric acid.

13. The process according to claim 12, wherein the amount of the acid is from 0.1 to 1.5 molar equivalents in respect to anastrozole.

14. The process according to claim 12, wherein the concentration of the acid is between 1-2% based on the amount of water.

15. The process according to claim 12, wherein the aqueous acid solution further comprises a water miscible C1-C4 aliphatic alcohol.

16. The process according to claim 15, wherein the concentration of the alcohol in the solution is from 40 to 60 vol %.

17. The process according to claim 11, wherein the formed solution further comprises a water miscible dipolar aprotic solvent.

18. The process according to claim 17, wherein said anastrozole base is contained in said dipolar aprotic solvent when combined with said aqueous acidic solution.

19. A process for purification of anastrozole, which comprises:
combining anastrozole base, water, and a water miscible C1-C4 aliphatic alcohol to form a solution; and
crystallizing anastrozole base from said solution.

20. The process according to claim 19, wherein the concentration of the alcohol in the solution is from 20 to 80 vol % and said alcohol is methanol.

21. The process according to claim 20, wherein said solution does not contain hydrochloric acid and wherein said methanol is contained in a concentration of 40% to 60%.

22. A process for making a pharmaceutical grade anastrozole comprising the steps of:

a) providing anastrozole in a reaction mixture by the condensation of the chloromethyl-compound of the formula (6) or bromomethyl-compound of formula (3):

(6)

CH$_2$Cl

NC     CN
H$_3$C     CH$_3$
   CH$_3$     CH$_3$ (3)

CH$_2$Br

NC     CN
H$_3$C     CH$_3$
   CH$_3$     CH$_3$ with sodium 1,2,4-triazole in a water miscible dipolar aprotic solvent;

b) adding water and hydrochloric acid to the anastrozole-containing reaction mixture and precipitating crude anastrozole base therefrom;

c) dissolving said crude anastrozole base in a mixture of water and a water miscible C1-C4 aliphatic alcohol in the presence of max. 1.5 molar equivalents of HCl and crystallizing anastrozole base to form purified anastrozole; and d) recrystallizing one or more times the purified anastrozole from a mixture of water and water miscible C1-C4 aliphatic alcohol to form anastrozole base in a purity of at least 99.97% and less than 0.1% of isoanastrozole.

23. The process according to claim 22, wherein the dipolar aprotic solvent is dimethyl formamide or dimethyl acetamide.

24. The process according to claim 22, wherein the aliphatic alcohol in steps (c) and (d) is methanol.

25. The process according to claim 22, wherein the concentration of alcohol in steps (c) end (d) is from 20 to 80 vol %.

26. The process according to claim 24, wherein said step (c) is carried out twice before step (d) is performed.

27. A process for purifying anastrozole, which comprises hydrolytically precipitating anastrozole from an acidic aqueous media.

28. A process for purifying anastrozole, which comprises:
(a) recrystallizing anastrozole base from an aqueous-based solvent system that comprises water, hydrochloric acid, optionally a water miscible C1-C4 aliphatic alcohol, and optionally a dipolar aprotic solvent; and/or
(b) recrystallizing anastrozole base from an aqueous-based solvent system that comprises water and a water miscible C1-C4 aliphatic alcohol but does not contain hydrochloric acid.

* * * * *